United States Patent [19]

Braverman

[11] Patent Number: 5,342,410
[45] Date of Patent: * Aug. 30, 1994

[54] APPARATUS AND METHOD FOR INCREASING THE AMPLITUDE OF P300 WAVES IN THE HUMAN BRAIN

[76] Inventor: Eric Braverman, 844 Rte. 518, Skillman, N.J. 08558

[*] Notice: The portion of the term of this patent subsequent to Nov. 17, 2009 has been disclaimed.

[21] Appl. No.: 759,945

[22] Filed: Sep. 16, 1991

Related U.S. Application Data

[63] Continuation-in-part of Ser. No. 593,067, Oct. 5, 1990, Pat. No. 5,163,446.

[51] Int. Cl.$^5$ .............................................. A61N 1/36
[52] U.S. Cl. ............................................. 607/58; 607/1; 607/2; 607/45; 607/46; 600/26
[58] Field of Search .......... 600/26; 128/419 S, 419 R, 128/421, 783, 791, 796, 907; 606/32–34; 607/1, 2, 45, 46, 58

[56] References Cited

U.S. PATENT DOCUMENTS

| | | | |
|---|---|---|---|
| 4,509,521 | 4/1985 | Barry | 128/421 |
| 4,785,813 | 11/1988 | Petrofsky | 128/421 |
| 5,163,444 | 11/1992 | Braverman | 128/783 |

FOREIGN PATENT DOCUMENTS

| | | | |
|---|---|---|---|
| 1286220 | 1/1987 | U.S.S.R. | 128/421 |
| 1489719 | 6/1989 | U.S.S.R. | 128/421 |

OTHER PUBLICATIONS

"The Relax Pak", Neuro Systems Incorp., 1986.

Electrosleep, Lewis and Williams; M.D., 13 Jan. 66, p. 40.
CES Labs 100 Hz User's Manual, 1989, all pages.

Primary Examiner—Randall L. Green
Assistant Examiner—P. Zuttarelli
Attorney, Agent, or Firm—Mathews, Woodbridge & Collins

[57] ABSTRACT

A cranial electrotherapy stimulation ("CES") device which generates periodic electrical signals is connected between the forehead and wrist area of a human being in order to affect electrical activity in the brain and thereby decrease the individual's craving for controlled substances such as alcohol and drugs and reduce anxiety, insomnia and depression. A portable, cranial electrical stimulator is preferably mounted adjacent the arm area or worn about the waist of a patient. A first electrode is attached to the forehead of the patient, preferably above the bridge of the nose between the eyes, and a second electrode is attached to the wrist area of one arm, preferably at the radial artery. Periodic electrical pulses having a waveform with a current amplitude in the range of 0.1 to 60 mA, a voltage of approximately 40–60 volts, a frequency of approximately 0.1 to 400 Hz, and a pulse width approximately 0.2 to 2 milliseconds at a 20% duty cycle are applied for at least 20 minutes between the forehead and wrist electrode. As a result, electrical activity in the brain is affected, in particular, the amplitude of P300 electrical brain activity is increased. Since decreased P300 activity is associated with increased patient interest in drugs and alcohol, the use of the CES in the is way makes it less likely that the patient will desire such controlled substances.

16 Claims, 4 Drawing Sheets

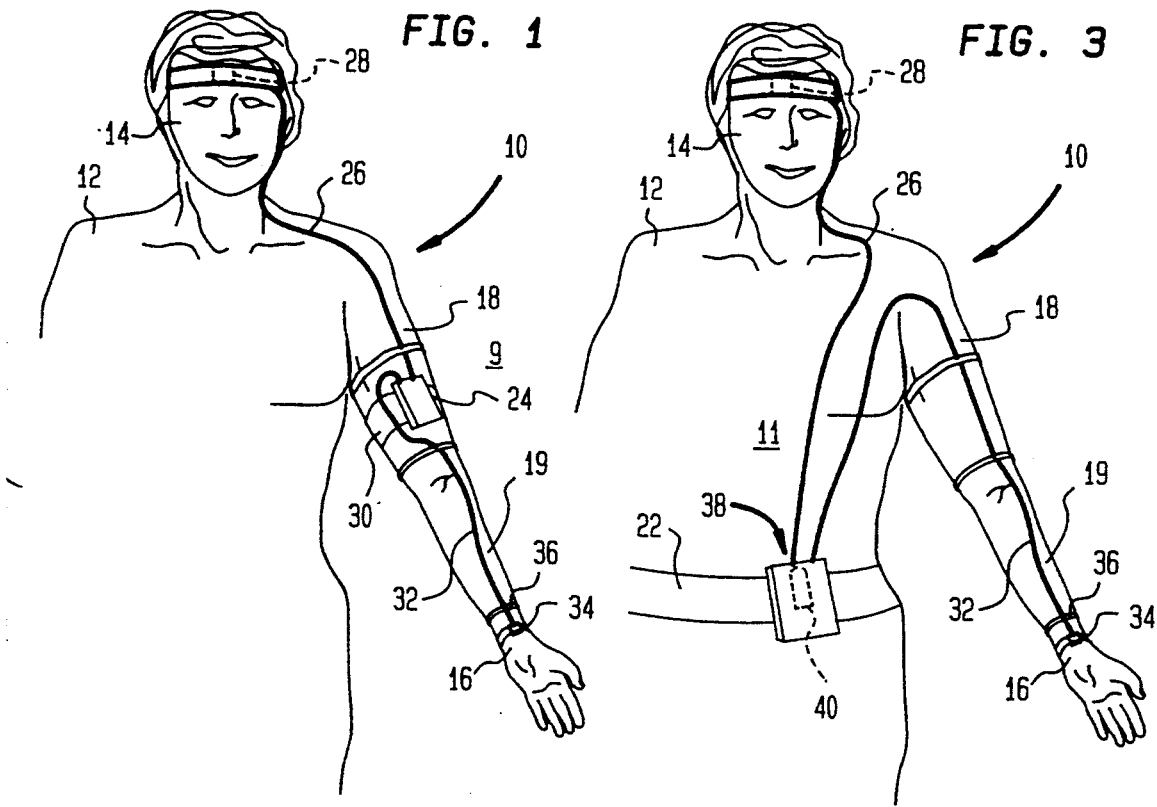
FIG. 1
FIG. 3
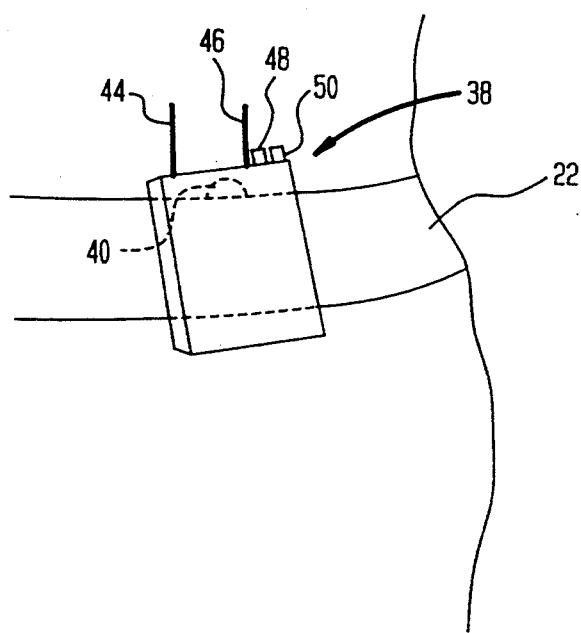
FIG. 4
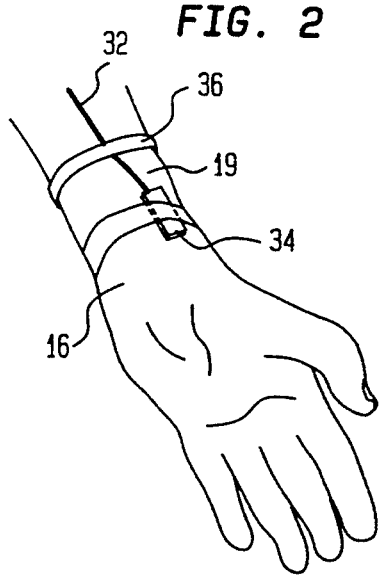
FIG. 2

APPARATUS AND METHOD FOR INCREASING THE AMPLITUDE OF P300 WAVES IN THE HUMAN BRAIN

CROSS-REFERENCE TO RELATED APPLICATIONS

This application is a continuation-in-part of copending application Ser. No. 07/593,067, filed on Oct. 5, 1990 entitled "Apparatus and Method for Increasing the Amplitude of P300 Waves in the Human Brain" now U.S. Pat. No. 5,163,444.

BACKGROUND OF THE INVENTION

1. Field of the Invention

The invention relates to a method and apparatus for increasing electrical brain activity, in particular the amplitude of P300 waves, thereby decreasing cravings for addictive substances by providing cranial electrical stimulation between the forehead and wrist area of a patient.

2. Description of the Related Art

P300 waves are electrical waves which occur in the human brain. They are a cognitive evoked potential in response to a stimulus to the brain known as an "oddball paradigm of beeps." The P300 wave occurs at approximately 300 ms from the initial stimulation of a patient with the oddball paradigm and are measured using a quantified EEG machine such as a device known as a BEAM ("Brain Electrical Activity Map"). The "P" stands for "Positive." Various researchers have correlated a diminished activity of P300 waves with an increase in craving for alcohol and other addictive drugs. See e.g., Begleiter & Porjesz, *Neuroelectric Processes in Individuals at Risk for Alcoholism*, Alcohol & Alcoholism, Vol, 25:251-256 (1990); Begleiter Porjesz Rawlings & Echardt *Auditory Recovery Function and P3 in Boys at High Risk for Alcoholism*, Alcohol Vol 4:315-321 (1987); Begleiter & Porjesz, *The P300 Component of the Event-Related Brain Potential in Psychiatric Patients*, Evoked Potential, 529-535, New York: Alan R. Liss, Inc. (1986); Whipple, Parker & Noble, *An Atypical Neurocognitive Profile in Alcoholic Fathers and Their Sons*, Journal of Studies on Alcohol, Vol. 43:240-244 (1988); Polich, Burns, & Bloom, *P300 and the Risk for Alcoholism*, Clinical and Experimental Research, Vol. 12:248-254 (1988); Schukits, Gold, Croot, Finn & Polich, *P300 Latency After Ethanol Ingestion in Sons of Alcoholics and in Controls*, Biological Psychiatry, Vol. 24:310-315 (1988); O'Connor, Hesselbroch, Tasman, Depalma, *P3 Amplitudes in Two Distinct Tasks are Decreased in Young Men with a History of Paternal Alcoholism*, Alcohol Vol. 4:323-330 (1987). The amplitude of P300 waves is a measure of concentration, attention and anxiety. An increase in P300 wave amplitude probably has applications beyond a decrease in cravings for alcohol and drugs (i.e., reduction of anxiety, depression and insomnia).

Cranial Electrotherapy Stimulation ("CES") is a term applied by the U.S. Food and Drug Administration ("FDA") to the transcranial application of small amounts of electricity, usually less than 1.5 mA at 100 Hz, to the head of a human being. It was originally used in the 1960's to induce sleep.

Prior art applications of CES devices have involved the use of higher frequencies, e.g., Liss, whose device operates at 15 kHz, the electrodes being attached to the head at the temples by means of a headband device. Researchers have shown that CES at 100 Hz is beneficial to alcoholics and drug abusers when attached to the mastoids. See, e.g., Smith, *Cranial Electrotherapy Stimulation, Neural Stimulation*, Vol. II: 129-150, Boca Raton, Fla., CRC Press Inc. (1985); Schmitt, *Capo Frazier & Cranial Electrotherapy Stimulation Treatment of Cognitive Brain Dysfunction Chemical Dependence*, Journal of Clinical Psychiatry, Vol. 45:60-63 (1984); Smith, *Confirming Evidence of an Effective Treatment of Brain Dysfunction in Alcoholic Patients*, Journal of Nervous and Mental Disease, Vol. 170:275-78 (1982) and Smith & Day, *The Effects of Cerebral Electrotherapy on Short-Term Memory Impairment in Alcoholic Patients*, International Journal of the Addictions, Vol. 12(4):574-82 (1977). However, the placement of the electrodes on the head and arm, and, more particularly above the eyes and on the wrist, as disclosed herein, as opposed to the mastoids has greater beneficial effects on brain waves, in particular, increasing P300 wave amplitude in alcoholics and drug abusers. Both positions tend to normalize brain waves, but the placement of the electrodes on the forehead and wrist has the added beneficial effect on P300 wave amplitude.

The FDA has approved numerous CES devices for the treatment of anxiety, insomnia and depression. Several thousand patients are treated using CES devices annually in America. Existing CES devices are used by connecting electrodes to patients' mastoids, earlobes or temples. There have been anecdotal reports of studies using the CES device on the leg and the head. There have also been studies in which the electrodes have been connected to the temples, forehead, and eyelids, but not simultaneously to the wrist and the forehead. The connection of a CES device between the head and the arm to increase P300 wave activity does not appear to be taught or suggested by the prior art.

SUMMARY OF THE INVENTION

Briefly described the invention comprises a cranial electrotherapy stimulation ("CES") device which generates a substantially periodic current waveform having a frequency approximately between 50 and 300 Hz, a current amplitude in the range of 0 to 400 mA, a voltage of approximately 40-60 volts, a pulse width in the range of 0.20 to 2 milliseconds and a duty cycle of about 20%. The substantially periodic waveform may be of a number of shapes including sinusoidal or rectangular. Within the broad range described above it has the following preferred characteristics: pulse width approximately 0.25 milliseconds; frequency 75-125 Hz; and, amplitude approximately 0.1-60 mA; voltage approximately 40-60 volts and a duty cycle of about 20%. The CES device has two outputs, one of which is connected to the head and the other of which is connected to the arm of a patient, preferably above the eyes and on the wrist. The patient is stimulated with the device for between 20 minutes and two hours. Such stimulation results in an increase in the amplitude of P300 waves in the brain which in turn is associated with a decrease in cravings for alcohol and drugs.

The invention may be more fully understood by reference to the following drawings.

BRIEF DESCRIPTION OF THE DRAWINGS

FIG. 1 is a view of a person using the preferred embodiment of the invention with the CES device carried on the bicep.

FIG. 2 is a detail showing the wrist electrode connected to the person's wrist at the radial artery.

FIG. 3 is a view of an alternative embodiment of the invention in which the CES device is worn on a belt around the waist.

FIG. 4 shows the CES device attached to the waist of the person by means of a belt.

DETAILED DESCRIPTION OF THE PREFERRED EMBODIMENT

Figure 5:
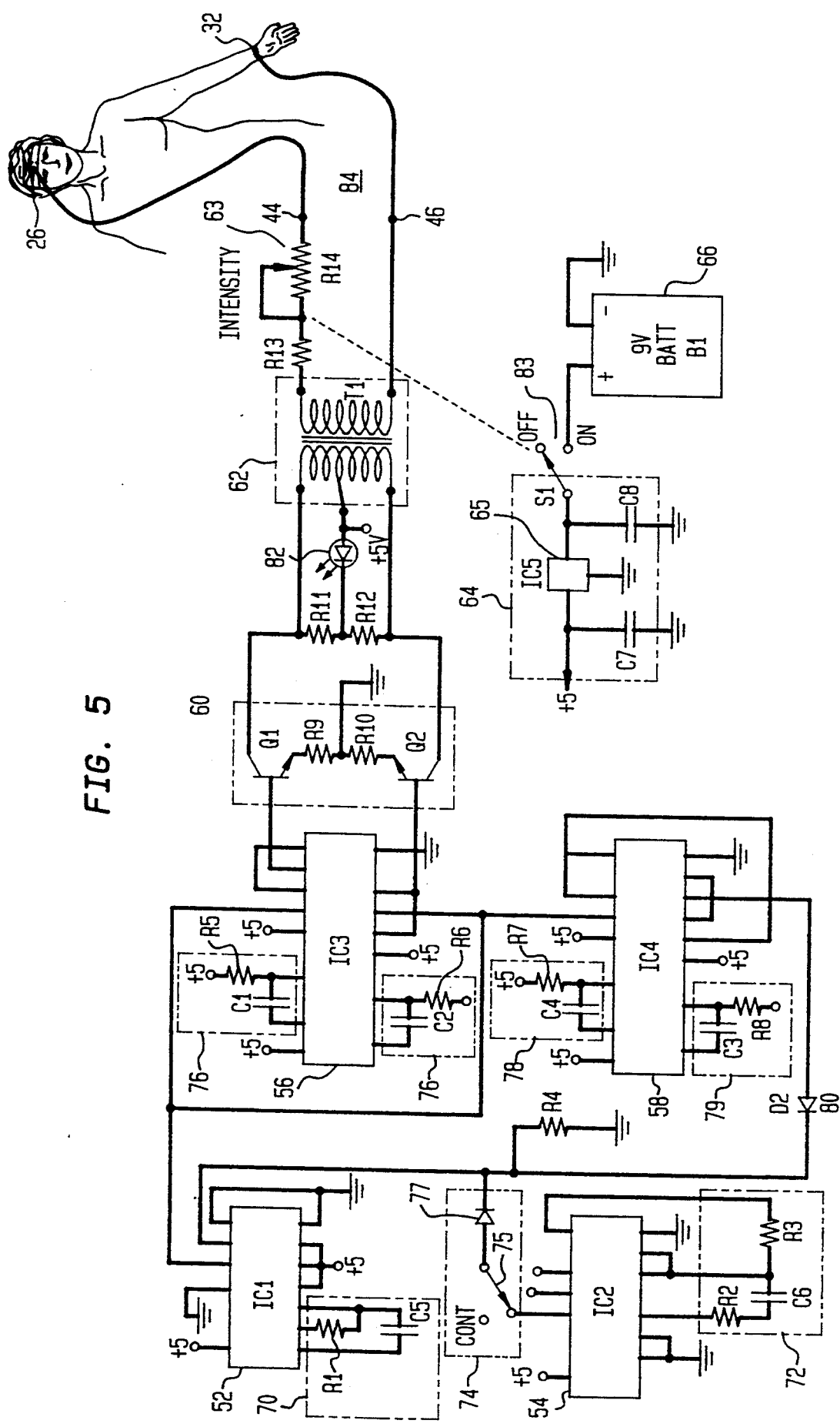
FIG. 5 is a schematic diagram of the electrical circuitry of the CES.

During the course of this description like numbers will be used to indicate like elements according to the different views of the invention.

FIG. 1 illustrates the preferred embodiment 9 of invention 10. ACES device 24 is shown attached to the arm 18 of patient 10 by means of strap 30. In FIG. 3, which illustrates an alternative embodiment 11 of invention 10, the CES device 38 is attached to the waist of patient 10 by means of clip 40 and belt 22.

FIG. 4 illustrates the CES device 38 attached to the waist of patient 10 as in the alternative embodiment 11. FIG. 4 also illustrates the output ports 44 and 46 of CES device 38, switch 48, which is used to turn the CES device on and off, and control knob 50, which is used to adjust the output of the device 38. Output ports 44 and 46, switch 48 and control knob 50 are present (but not shown) in both embodiments 9 and 11.

An example of an acceptable portable CES device 24 or 38 is the unit marketed under the name "Healthpax" by Health Directions Inc. of 411 W. Trenton Ave., Morrisville, Pa. 19067. Similar devices are manufactured by various other companies such as CES Labs, 14770 N.E. 95h St., Redmond, Wash. 98052; NeuroSystems, Inc., 11235 Pegasus, Suite E-102, Dallas, Tex. 75238 and Neurotek, Inc., 750 E. Campbell Rd., Suite 600, Richardson, Tex. 75081. Other devices generating waveforms of various shapes, frequencies, amplitudes and duty cycles may also be used. For example, sine waves have been shown to produce similar effects.

In both embodiments 9 and 11, the head electrode 28 is attached to the patient's head 14, preferably at a point immediately above the bridge of the nose and between the eyes. A wrist electrode 34 is attached to the wrist 16 of the patient, preferably at the radial artery. However, the electrodes may also be placed anywhere on the head, above the eyes and on the arm near an artery. The wrist electrode preferably acts as an electrical ground point. The head electrode 28 and the wrist electrode 34 are respectively connected to the output ports 44 and 46 of the CES device 38 or 24 (depending on the embodiment) by means of head electrode wire 26 and wrist electrode wire 32.

The head electrode 28 and the wrist electrode 34 are conventional medical gel electrodes such as those available from Transcutek of 13100 S. 300 E. Draper, Utah 84020 or Mr. Electrode, Beck Lee Co., P.O. Box 425, Stratford, Conn. 06497. Alternatively, the head electrode 28 may be a copper conducting wire, held in place by means of a headband fastened by Velcro ® strips or an elastic material. The wrist electrode 34 may also be a copper conducting wire, held in place by a wrist band secured by Velcro ® strips or an elastic material. While head electrode 28 and wrist electrode 34 are illustrated on top of the skin, it will be appreciated by those of ordinary skill in the art that implant electrodes below the skin are also possible.

Once the head electrode 28 and wrist electrode 34 are in place, the CES device is switched by means of switch 48 on CES device 38 or 24. The output current of the CES device is adjusted to between 0.1 and 1.5 mA using the control knob 50 on the CES device. However, currents in the range of 0.1 to 60 mA and up to 400 mA may also be used. The output current level is selected depending on the patient's comfort level. The highest level tolerable to the patient is preferable. The patient is stimulated in this way for between 20 minutes and two hours. After approximately 20 minutes there are likely to be significant changes in the activity of various electrical waves in the patient's brain. In particular, the amplitude of P300 waves is likely to increase significantly after approximately 40 minutes of stimulation in this way. Further applications of stimulation over a period of weeks have an increased beneficial effect.

FIG. 5 is an electrical schematic diagram of the portable, internal electrical circuit of the preferred embodiment of CES device 28 or 34. The components of the circuit are mounted on an appropriately laid out printed circuit board. This circuit is disclosed by way of example only. Those of ordinary skill in the art are able to construct similar circuits to produce waveforms of various frequencies, shapes, amplitudes and/or duty cycles without undue experimentation.

Integrated circuit 52 is an astable multivibrator producing a square wave output between 0 and 5 volts, available from Harris Semiconductor, Inc., Part No. CD4047B. Resistor-capacitor combination 70 determines the frequency of the output of integrated circuit 52. Integrated Circuit 54 is an electronic counter with a built in oscillator to produce time delays to control the amplitude of the output waveform of the CES device 28 or 34. Integrated circuit 54 is available from Harris Semiconductor, Inc., Part No. CD4521B. Resistor-capacitor combination 72 controls the time of application of the output waveform. Integrated circuit 54 is controlled by timer 74. Timer 74 includes a switch 75, which is a standard single pole four position switch available from Mouser Electronics, and diode 77 which is a germanium low forward drop diode available from National Semiconductor Corp., Part No. IN4305. Integrated circuit 56 is a dual one shot circuit consisting of two single pulse generators to generate output pulses. Integrated circuit 56 produces a series of two positive pulses followed by two negative pulses. Integrated circuit 56 is available from Harris Semiconductor, Inc., Part No. CD4538B. Resistor capacitor combination 76 controls the pulse width and time delay of the output pulses. Integrated circuit 58 is a second dual one shot circuit and is identical to integrated circuit 56. Integrated circuit 58 controls the time that the output pulses are on or off and produces the 20% duty cycle. Resistor-capacitor combinations 78 and 79 control the pulse width and time delay. Transistor-resistor combination 60 amplifies the output current of integrated circuit 56 in order to drive transformer 62. The transistors used in transistor-resistor combination 60 are standard NPN transistors available from Motorola Inc., Part No. 2N2222. Transformer 63 is an open frame transformer available from Mouser Electronics, Part No. 422TM002. Transformer 62 isolates the output and steps up the voltage to 40 volts peak (80 volts peak to peak). Potentiometer 62 is a standard 50 K potentiometer which controls the current output intensity. Voltage regulator 64 comprises a voltage regulator integrated circuit 65 which produces a regulated output of 5 volts, available from Linear Technology Corp Part No LM2931Z5. Battery 66 is a standard 9 volt alkaline battery. Diode 80 is a germanium low forward drop diode available from National Semiconductor Corp., Part No. 1N4305. Light emitting diode 82 is a standard light emitting diode available from Mouser Electronics, Part No. F350001. Light emitting diode 82 is lit when the device is switched on by means of on/off switch 83.

The output 84 comprises two standard electrical pin-jacks to which output ports 44 and 46 are connected.

The values of the various resistors and capacitors are as follows:

| | | |
|---|---|---|
| $R_1 = 10K\Omega$ | $R_{10} = 47K\Omega$ | $C_5 = 0.1\ \mu F$ |
| $R_2 = 1M\Omega$ | $R_{11} = 1K\Omega$ | $C_6 = 0.1\ \mu F$ |
| $R_3 = 75K\Omega$ | $R_{12} = 1K\Omega$ | $C_7 = 0.1\ \mu F$ |
| $R_4 = 100\Omega$ | $R_{13} = 4.3K\Omega$ | $C_8 = 0.1\ \mu F$ |
| $R_5 = 47K\Omega$ | $R_{14} = 50K\Omega$ | |
| $R_6 = 47K\Omega$ | $C_1 = 0.1\mu F$ | |
| $R_7 = 36K\Omega$ | $C_2 = 0.1\mu F$ | |
| $R_8 = 150\Omega$ | $C_3 = 0.1\mu F$ | |
| $R_9 = 47\Omega$ | $C_4 = 0.1\mu F$ | |

The power rating for all resistors is ⅛ W. The voltage rating for all capacitors is 20 V minimum.

Figure 6:
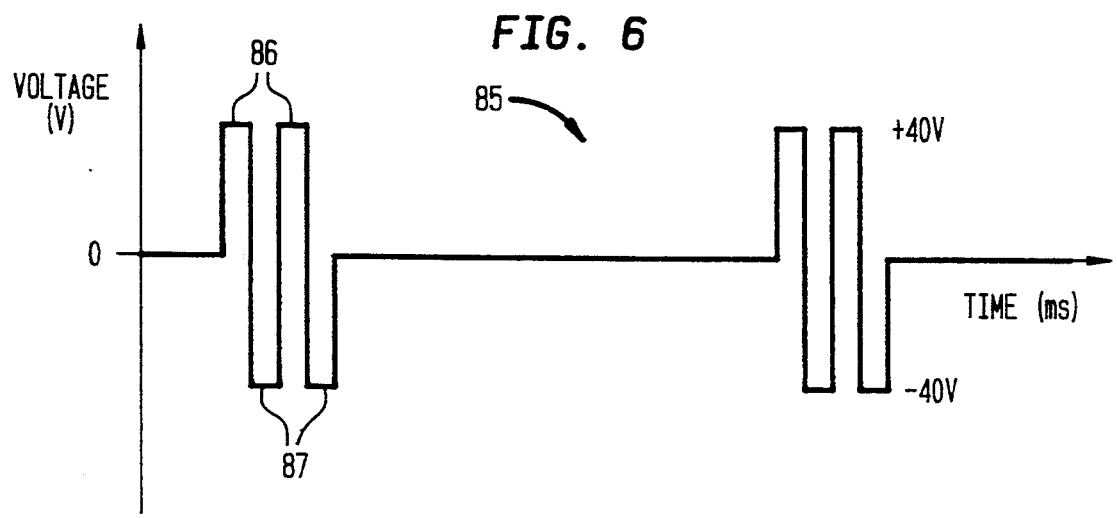
FIG. 6 is a graph of a preferred rectangular waveform output of the CES device.
Figure 9:
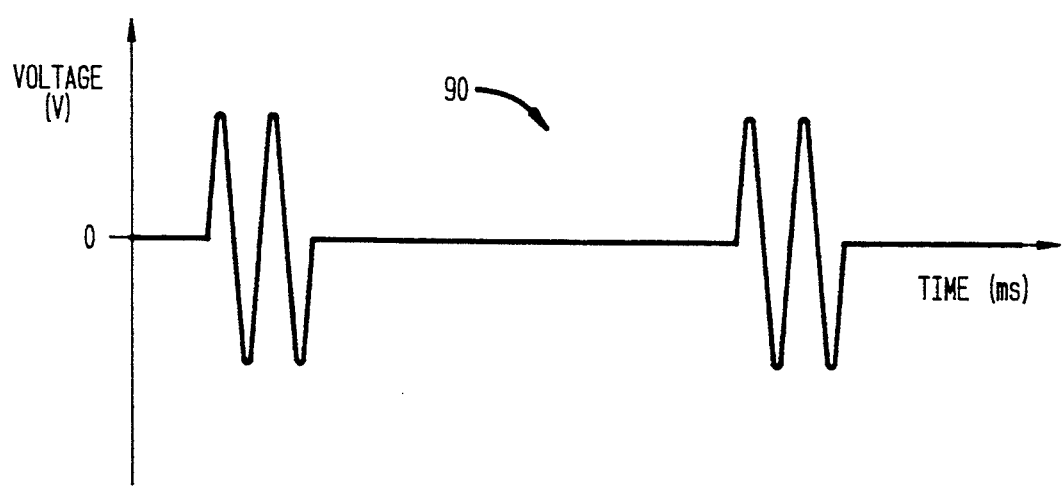
FIG. 9 is a graph of an alternative sinusoidal waveform for the CES device.

FIG. 6 shows the preferred current waveform output 85 of the CES device at the output 84 under no-load conditions. A single cycle of the current waveform 85 has a period of 12.2 ms. A single cycle consists of two peaks 86 of amplitude 40 V, two troughs 87 of amplitude −40 V and a rest period at 0 V of 7.8 ms. Each peak and each trough has a duration of 4.4 ms. Waveforms of different shape, frequency, amplitude and duty cycles may also be used. For example, a sinusoidal waveform 90 such as shown in FIG. 9 would also be satisfactory.

Experiments with patients using the invention and control experiments have yielded the following data.

In one study, 30 patients who were alcoholics or children of alcoholics, were each stimulated for 40 minutes at 100 Hz with a Healthpax CES attached to the forehead and wrist. P300 waves were measured at the central and parietal midline regions of the head. The amplitude of P300 waves as raised from 5.98±3.6 μv to 8.45±4.7 μv. These results are tabulated on Table A.

TABLE A

CHANGE IN TIME AND AMPLITUDE OF P300 WAVEFORM AT CZ AND PZ ELECTRODE IN CHILDREN OF ALCOHOLICS AND ALCOHOLICS (N = 30)

| | PRIOR TO STIMULATION | AFTER STIMULATION |
|---|---|---|
| Time (msec) | 318.4 ± 26.0 | 329.3 ± 33.2 |
| P300 Amplitude | 5.98 ± 3.6 | 8.45* ± 4.7 |

TABLE A-continued

CHANGE IN TIME AND AMPLITUDE OF P300 WAVEFORM AT CZ AND PZ ELECTRODE IN CHILDREN OF ALCOHOLICS AND ALCOHOLICS (N = 30)

| | PRIOR TO STIMULATION | AFTER STIMULATION |
|---|---|---|
| (microvolts) | | |

*p < .0001

Sixty seven subjects with neuropsychiatric disorders were selected as they entered a clinic for brain electrical activity mapping (BEAM) testing. All patients provided informed consent participation. They were each administered the full BEAM test, then wore the Health-Pax (a CES device with a 20% duty cycle, 100 pulses/sec. (Hz) 1.5 mA, square wave, no DC bias pulse width duration of 2 ms) for 40 minutes as adjusted to maximum comfort by patients, with electrode placements on the forehead between the eyes and on the radial pulse of the left wrist. Immediately following the 40 minutes of CES treatment, all subjects were given a second BEAM including cognitive evoked potentials (P300) by odd ball paradigm. The results of this study are shown in TABLE B.

TABLE B

INCREASE IN AMPLITUDE OF P300 AT MAXIMUM VOLTAGE IN 67 PATIENTS FOLLOWING 40 MINUTES OF CRANIAL ELECTRICAL STIMULATION

| | PRIOR TO STIMULATION N = 67 | AFTER STIMULATION N = 67 |
|---|---|---|
| Time (msec) | 326 ± 26 | 325 ± 26 |
| P300 Amplitude (microvolts) | 6.92 ± 3.0 | 8.8 ± 7* |

* a P < .00001 increase in voltage occurred.

Sixty three subjects of neuropsychiatric patients, all with a history of addiction disorders, (32 females and 34 males), ranging in age from 8 to 81 years (means, age 41.59), were selected as they entered the clinic for brain electrical activity mapping (BEAM) testing. They were each administered the full BEAM test, then wore a 3M CES device (0.25% duty cycle, 100 pulses per sec (Hz) amplitude of 60 mA at peak, pulse width duration of 2.5 milliseconds) adjusted to maximum level of comfort by patients for 40 minutes. Subjects were instructed to modulate the amplitude to maximum level of comfort, with electrode placements on the forehead between eyes and on the radial pulse of left wrist. Immediately following the 40 minutes of CES treatment, all subjects were given a second BEAM including cognitive evoked potentials (P300) by odd ball paradigm. The results are tabulated in Table C.

TABLE C

INCREASE IN AMPLITUDE OF P300 AT PZ VOLTAGE IN 63 PATIENTS FOLLOWING 40 MINUTES OF CRANIAL ELECTRICAL STIMULATION

| | PRIOR TO STIMULATION N = 63 | AFTER STIMULATION N = 63 |
|---|---|---|
| Time (msec) | 325 ± 26 | 332 ± 36 |
| P300 Amplitude (microvolts) | 6.9 ± 3.0 | 7.9 ± 7* |

* a P < .01 increase in voltage occurred.

Sixty three subjects neuropsychiatric patients (32 females and 34 males), ranging in age from 8 to 81 years (mean age 41.59), were selected as they entered the clinic for brain electrical activity mapping (BEAM) testing. All patients provided informed consent to participation and were each administered the full BEAM test, then wore a 3M CES device (0.25% duty cycle, 100 pulses per sec (Hz) amplitude of 50 mA at peak, pulse width duration of 2.5 ms) for 40 minutes and adjusted to maximum level of comfort by patients. Subjects were instructed to modulate the amplitude at maximum level of comfort with electrode placements on the forehead between the eyes and radial pulse of left wrist. Immediately following the 40 minutes of CES treatment, all subjects were given a second BEAM including cognitive evoked potentials (P300) by odd ball paradigm. The results are tabulated in Table D.

TABLE D

INCREASE IN AMPLITUDE OF P300 AT MAXIMUM VOLTAGE IN 63 PATIENTS FOLLOWING 40 MINUTES OF CRANIAL ELECTRICAL STIMULATION

|  | PRIOR TO STIMULATION N = 63 | AFTER STIMULATION N = 63 |
|---|---|---|
| Time (msec) | 325 ± 26 | 332 ± 36 |
| P300 Amplitude (microvolts) | 8.2 ± 3.0 | 9.0 ± 3.4* |

* a $P < .01$ increase in voltage occurred.

The results illustrated in Tables B, C and D were generated by the 3M CompTenz ™ Dual Channel TENS Stimulator Kit Catalog Number 6820.

A further sample of 16 children of alcoholics and alcoholics were stimulated for 40 minutes at 100 Hz with Healthpax devices. P300 amplitudes increased from 4.03±3.4 μv. to 6.17±4.2 μv. These results are tabulated in Table E.

TABLE E

CHANGE IN AMPLITUDE OF P300 WAVEFORM AT FZ ELECTRODE IN CHILDREN OF ALCOHOLICS AND ALCOHOLICS (N = 16)

|  | PRIOR TO STIMULATION | AFTER STIMULATION |
|---|---|---|
| Time (msec) | 4.03 ± 3.4 | 6.17* ± 4.2 |
| P300 Amplitude (microvolts) | 314.2 ± 27.7 | 317.9 ± 28.4 |

*$p < .001$

After 40 minutes of stimulation with Healthpax CES's attached to the foreheads and wrists of 14 brain diseased patients, P300 waves increased from 7.0±4.1 μV to 9.9±6.1 μv. These results are tabulated on Table F.

TABLE F

MODIFICATION OF P300 WAVEFORM IN ORGANIC BRAIN DISEASED PATIENTS WEARING CES IN LEFT WRIST/CENTRAL FOREHEAD POSITION FOR 40 MINUTES (N = 14)

|  | PRIOR TO STIMULATION | AFTER STIMULATION |
|---|---|---|
| Time (msec) | 308 ± 24 | 317.1 ± 26 |
| P300 Amplitude (microvolts) | 7.0 ± 4.1 | 9.9* ± 6.1 |

* $p < .03$ by paired T test

Table G shows the increase in P300 wave amplitude in a sample of 29 psychiatric patients, children of alcoholics and drug abusers after application of the invention for 40 minutes. As may be seen, the amplitude of P300 waves increased from 7.05±4.4 μv to 9.18±4.5 μv.

TABLE G

MODIFICATION OF P300 IN PSYCHIATRIC PATIENTS, CHILDREN OF ALCOHOLICS AND DRUG ABUSERS AFTER 40 MINUTES OF WEARING CES IN THE WRIST/FOREHEAD POSITION (N = 29)

|  | PRIOR TO STIMULATION | AFTER STIMULATION |
|---|---|---|
| Time (msec) | 316.3 ± 23.7 | 318.2 ± 27.8 |
| Amplitude (microvolts) | 7.05 ± 3.3 | 9.18* ± 4.5 |

* $p > .001$ paired T test

Figure 7:
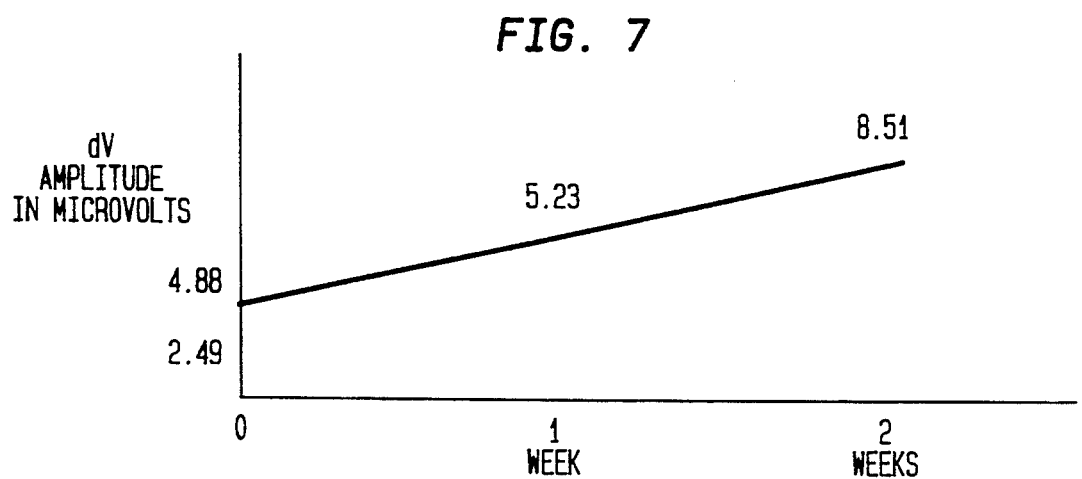
FIG. 7 is a graph showing increases in P300 wave amplitude of a 27 year old child of an alcoholic with a history of alcohol abuse after 40 minutes of stimulation using the invention over a period of two weeks.
Figure 8:
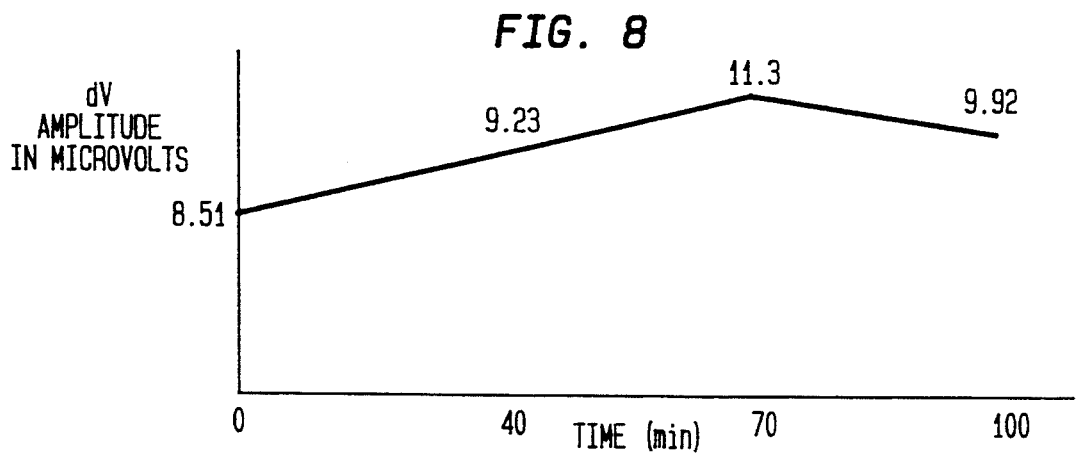
FIG. 8 is a graph showing the increase in P300 wave amplitude in a 27 year old child of an alcoholic with a history of alcohol abuse after 100 minutes of stimulation using the invention.

In one stimulated patient, the child of an alcoholic with a history of alcohol abuse, an increase in P300 amplitude from 2.49 to 8.51 μv was observed over a period of two weeks of daily treatment of such treatment for 40 minutes per day. These results are graphically represented in FIG. 7. In the same patient an increase in P300 amplitude from 8.51 to 11.3 μv was observed after a single period of 70 minutes of stimulation. These results are graphically represented in FIG. 8.

Other studies using different electrical frequencies, sham inputs and positioning the electrodes on the mastoids did not produce significant increases in P300 amplitudes.

A study involving 10 patients stimulated for 40 minutes each at 100 Hz using the Healthpax device via electrodes attached to the mastoids produced no significant change in P300 amplitude. These results are tabulated on TABLE H.

TABLE H

CHANGE IN TIME AND AMPLITUDE OF P300 WAVE FOLLOWING 40 MINUTES OF CES (HEALTH PAX) WORN ON MASTOIDS (N = 10)

|  | PRIOR TO STIMULATION | AFTER STIMULATION |
|---|---|---|
| Time (msec) | 329.2 ± 20.0 | 344.6 ± 22.2 |
| Amplitude (microvolts) | 11.2 ± 5.1 | 9.9 ± 2.3 |

A sham CES with no current output was applied to 10 patients for 40 minutes each, the electrodes being connected to the forehead and wrist. There was no significant increase in P300 amplitude in the patients. These results are tabulated on TABLE I.

TABLE I

DOCUMENTATION OF NO SIGNIFICANT CHANGE IN P300 WITH 40 MINUTES OF SHAM CES (N = 10)

|  | PRIOR TO APPLICATION | AFTER APPLICATION |
|---|---|---|
| Time (msec) | 336 ± 24 | 324 ± 27 |
| P300 Amplitude (microvolts) | 8.4 ± 3.8 | 8.4 ± 4.9 |

The foregoing results demonstrate the effectiveness of CES applied to the forehead and wrist in raising the level of P300 waves in alcoholics, children of alcoholics and brain diseased psychiatric patients.

It appears that a substantial increase in the amplitude of P300 activity can be achieved by a variety of different periodic waveforms including, but not necessarily limited to, rectangular or sinusoidal. Beneficial results are anticipated with periodic waveforms having the following characteristics: frequency in the range of 50 to 300 Hz; pulse width in the range 0.20 to 2.0 to 2.5 milliseconds, and amplitude in the range of 0–400 mA. It is unlikely that beneficial results would be obtainable above 400 mA in view of the fact that seizures may start to occur with amplitudes above 300 mA. The preferred range of periodic pulse characteristics is demonstrated to be approximately: frequency 75–125 Hz centered around approximately 100 Hz; pulse width approximately 0.25 milliseconds, a duty cycle of about 20%, a current amplitude of approximately 0–60 mA with slight preference for 15 mA and a voltage in the range of 40 to 60 volts. The results have clearly shown that oddball paradigm P300 waveforms can be inducted by the apparatus and methods disclosed. It is expected, however, that the invention can also be applied to other methods of involving P300 activity such as for example, by visual induction.

While the invention has been described with reference to the preferred embodiment thereof, it will be appreciated by those of ordinary skill in the art that modifications can be made to the parts and steps that comprise the invention without departure from the spirit and scope of the invention as a whole. Such modifications may include but not be limited to, changing the frequency, amplitude, duty cycle and shape of the waveform.

I claim:

1. A system for providing electrical stimulation to a human being and thereby increasing amplitude of P300 wave activity in a brain of said human being, said human being having a forehead and a wrist, said system comprising:
    a source for generating a substantially periodic electrical waveform;
    a first electrode means for connecting said source to the forehead of said human being; and
    a second electrode means for connecting said source to the wrist of said human being wherein said source produces said substantially periodic waveform having an amplitude in a range of approximately 0.1 to 400 mA, a frequency in a range of 50 to 300 Hz and a pulse width of greater than 0.2 milliseconds and less than 2.0 milliseconds.

2. A system of claim 1 wherein said source comprises a cranial electrotherapy stimulation device.

3. A method of increasing amplitude of P300 waves in a skull of a human being, said human being having a forehead and a wrist, comprising the steps of:
    attaching a first electrode to the forehead of said human being;
    attaching a second electrode to the wrist of said human being; and
    applying a substantially periodic electrical signal between said first electrode and said second electrode wherein said electrical signal has a frequency in a range of 50 to 300 Hz, an amplitude in a range of 0.1 to 60 mA, and a pulse width greater than 0.2 milliseconds and less than 2.0 milliseconds.

4. The method of claim 3 further comprising the step of:
    applying said electrical signal between said first and second electrodes for at least 20 minutes.

5. A method of increasing the amplitude of P300 waves in a brain of a human being, said human being having a head and wrist, comprising the steps of:
    attaching a first electrode means to the head of said human being;
    attaching a second electrode means to said wrist of said human being; and,
    applying between said first and second electrode means a substantially periodic waveform having a frequency in a range of 50 to 300 Hz, a current amplitude of approximately 0.1 to 400 mA, a voltage in a range of 40 to 60 volts, and a pulse width greater than 0.2 milliseconds and less than 20 milliseconds at a duty cycle of about 20% for at least 20 minutes.

6. The method of claim 5 wherein said head includes a forehead first electrode means is attached to said forehead of said human being.

7. The method of claim 5 wherein said head includes a forehead further comprising the step of:
    connecting said first electrode means to said forehead of said human being between eyes of said human being and above a bridge of the nose of said human being.

8. The method of claim 5 further comprising the step of:
    connecting said second electrode means to the wrist of said human being in the region of a radial artery of said wrist.

9. The method of claim 5 wherein said substantially periodic waveform has a frequency in a range of 70 to 125 Hz and an amplitude approximately in a range of 0.1 to 60 mA.

10. The method of claim 5 wherein said substantially periodic waveform has a substantially rectangular shape.

11. The method of claim 5 wherein said substantially periodic waveform has a substantially sinusoidal shape.

12. An apparatus for providing electrical stimulation to a human being and thereby increasing amplitude of P300 wave activity in a brain of said human being, said human being having a forehead and a wrist, said apparatus comprising:
    a source for generating a substantially periodic electrical waveform, said source including a cranial electrotherapy stimulation device which produces said substantially periodic waveform having an amplitude in a range of approximately 0.1 to 400 mA, a frequency in a range of approximately 50 to 300 Hz and a pulse width of greater than 0.20 milliseconds and less than 2.0 milliseconds;
    a first electrode means for connecting said source to the forehead of said human being; and
    a second electrode means for connecting said source to the wrist of said human being.

13. The apparatus of claim 12 wherein said first electrode means comprises an implant electrode.

14. The apparatus of claim 12 wherein said second electrode means comprises an implant electrode.

15. The apparatus of claim 12 further comprising:
    first connecting means for connecting said first electrode means to the forehead of said human being.

16. The apparatus of claim 12 further comprising:
    a second connecting means for connecting said second electrode means to the wrist of said human being.

* * * * *